US011892462B2

(12) United States Patent
Scialò et al.

(10) Patent No.: US 11,892,462 B2
(45) Date of Patent: Feb. 6, 2024

(54) ROBOTIC CONTROL FOR ASEPTIC PROCESSING

(71) Applicants: Particle Measuring Systems, Inc., Boulder, CO (US); Pharma Integration SRL, Siena (IT)

(72) Inventors: Giovanni Scialò, Frascati (IT); Davide Recchia, Frascati (IT); Claudio Bechini, Siena (IT)

(73) Assignees: Pharma Integration SRL, Siena (IT); Particle Measuring Systems, Inc., Boulder, CO (US)

( * ) Notice: Subject to any disclaimer, the term of this patent is extended or adjusted under 35 U.S.C. 154(b) by 548 days.

(21) Appl. No.: 17/151,899

(22) Filed: Jan. 19, 2021

(65) Prior Publication Data
US 2021/0223273 A1   Jul. 22, 2021

Related U.S. Application Data

(60) Provisional application No. 62/963,895, filed on Jan. 21, 2020.

(51) Int. Cl.
*G01N 35/00* (2006.01)
*B01L 3/00* (2006.01)
(Continued)

(52) U.S. Cl.
CPC .......... *G01N 35/0099* (2013.01); *B01L 3/502* (2013.01); *B25J 9/0009* (2013.01);
(Continued)

(58) Field of Classification Search
CPC ............ G01N 35/0099; G01N 1/2208; G01N 1/2273; B25J 9/0009; B25J 11/00; B01L 2200/0689; B01L 2300/04
See application file for complete search history.

(56) References Cited

U.S. PATENT DOCUMENTS 3,001,914 A   9/1961   Andersen
3,938,366 A   2/1976   Wertlake et al.
(Continued)

FOREIGN PATENT DOCUMENTS

CN   1218553 A   6/1999
CN   1275894 A   12/2000
(Continued)

OTHER PUBLICATIONS

Taiwan Decision of Rejection dated May 17, 2023 in Taiwan application No. 111150823.
(Continued)

*Primary Examiner* — Benjamin R Schmitt
(74) *Attorney, Agent, or Firm* — Leydig, Voit & Mayer, Ltd.

(57) ABSTRACT

Devices and methods for sampling, detecting and/or characterizing particles, for example, via collection, growth and analysis of viable biological particles such as microorganisms. Devices and methods of the invention include particle samplers and impactors including a sampling head comprising one or more intake apertures, a selectively removable cover, an impactor base connected to the sampling head, and one or more magnets fixed to the sampling head, the selectively removable cover and/or the impactor base. The one or more magnets allow for robotic manipulation of the impactor devices.

23 Claims, 4 Drawing Sheets

(51) Int. Cl.
  *C12M 1/00*    (2006.01)
  *C12M 1/12*    (2006.01)
  *C12Q 1/04*    (2006.01)
  *B25J 9/00*    (2006.01)
  *G01N 1/22*    (2006.01)
  *B25J 11/00*   (2006.01)

(52) U.S. Cl.
  CPC .............. *B25J 11/00* (2013.01); *C12M 23/22* (2013.01); *C12M 37/00* (2013.01); *C12Q 1/04* (2013.01); *G01N 1/2208* (2013.01); *G01N 1/2273* (2013.01); *B01L 2200/0689* (2013.01); *B01L 2300/04* (2013.01); *B01L 2300/168* (2013.01)

(56) References Cited

U.S. PATENT DOCUMENTS

| | | | |
|---|---|---|---|
| 4,594,715 A | 6/1986 | Knollenberg | |
| 4,798,465 A | 1/1989 | Knollenberg | |
| 4,827,779 A | 5/1989 | Marple et al. | |
| 4,893,928 A | 1/1990 | Knollenberg | |
| 5,032,721 A | 7/1991 | Bacon et al. | |
| 5,095,206 A | 3/1992 | Bacon, Jr. et al. | |
| 5,234,838 A | 8/1993 | Bacon, Jr. | |
| 5,282,151 A | 1/1994 | Knollenberg | |
| 5,283,199 A | 2/1994 | Bacon, Jr. et al. | |
| 5,440,916 A | 8/1995 | Stone et al. | |
| 5,671,046 A | 9/1997 | Knowlton | |
| 5,693,895 A | 12/1997 | Baxter | |
| 5,726,753 A | 3/1998 | Sandberg | |
| 5,751,422 A | 5/1998 | Mitchell | |
| 5,776,781 A | 7/1998 | Vardanega et al. | |
| 5,805,281 A | 9/1998 | Knowlton et al. | |
| 5,861,950 A | 1/1999 | Knowlton | |
| 5,889,589 A | 3/1999 | Sandberg | |
| 5,903,338 A | 5/1999 | Mavliev et al. | |
| 6,040,153 A | 3/2000 | Lemonnier | |
| 6,094,997 A | 8/2000 | Lemonnier | |
| 6,167,107 A | 12/2000 | Bates | |
| 6,240,768 B1 | 6/2001 | Lemonnier | |
| 6,246,474 B1 | 6/2001 | Cerni et al. | |
| 6,275,290 B1 | 8/2001 | Cerni et al. | |
| 6,435,043 B1 | 8/2002 | Ferguson et al. | |
| 6,472,203 B1 | 10/2002 | Gallup et al. | |
| 6,615,679 B1 | 9/2003 | Knollenberg et al. | |
| 6,651,404 B1 | 11/2003 | Hertfelder | |
| 6,709,311 B2 | 3/2004 | Cerni | |
| 6,859,277 B2 | 2/2005 | Wagner et al. | |
| 6,903,818 B2 | 6/2005 | Cerni et al. | |
| 6,928,892 B2 | 8/2005 | Storbeck et al. | |
| 6,945,090 B2 | 9/2005 | Rodier | |
| 7,030,980 B1 | 4/2006 | Sehler et al. | |
| 7,088,446 B2 | 8/2006 | Cerni | |
| 7,088,447 B1 | 8/2006 | Bates et al. | |
| 7,192,734 B2 | 3/2007 | Ohresser | |
| 7,208,123 B2 | 4/2007 | Knollenberg et al. | |
| 7,235,214 B2 | 6/2007 | Rodier et al. | |
| RE39,783 E | 8/2007 | Cerni et al. | |
| 7,334,453 B2 | 2/2008 | Trakumas et al. | |
| 7,456,960 B2 | 11/2008 | Cerni et al. | |
| 7,576,857 B2 | 8/2009 | Wagner | |
| 7,667,839 B2 | 2/2010 | Bates | |
| 7,745,469 B2 | 6/2010 | Dahmen et al. | |
| 7,746,469 B2 | 6/2010 | Shamir et al. | |
| 7,752,930 B2 | 7/2010 | Kreikebaum et al. | |
| 7,796,255 B2 | 9/2010 | Miller | |
| 7,916,293 B2 | 3/2011 | Mitchell et al. | |
| 7,973,929 B2 | 7/2011 | Bates | |
| 7,985,949 B2 | 7/2011 | Rodier | |
| 8,027,035 B2 | 9/2011 | Mitchell et al. | |
| 8,109,129 B2 | 2/2012 | Gorbunov | |
| 8,154,724 B2 | 4/2012 | Mitchell et al. | |
| 8,174,697 B2 | 5/2012 | Mitchell et al. | |
| 8,427,642 B2 | 4/2013 | Mitchell et al. | |
| 8,474,335 B2 | 7/2013 | Vellutato, Jr. | |
| 8,689,648 B1 | 4/2014 | Heff | |
| 8,800,383 B2 | 8/2014 | Bates | |
| 8,869,593 B2 | 10/2014 | Gorbunov et al. | |
| 9,121,845 B2 | 9/2015 | Vellutato, Jr. | |
| 9,513,278 B2 | 12/2016 | Vellutato, Jr. | |
| 9,592,609 B2 | 3/2017 | LaFary et al. | |
| 9,631,222 B2 | 4/2017 | Ketcham et al. | |
| 9,638,665 B2 | 5/2017 | Gorbunov | |
| 9,682,345 B2 | 6/2017 | Gromala et al. | |
| 9,695,458 B2 | 7/2017 | D'antonio et al. | |
| 9,808,760 B2 | 11/2017 | Gromala et al. | |
| 9,810,558 B2 | 11/2017 | Bates et al. | |
| 9,885,640 B2 | 2/2018 | Ketcham et al. | |
| 9,933,351 B2 | 4/2018 | Kent et al. | |
| 9,989,462 B2 | 6/2018 | Lumpkin et al. | |
| 10,060,837 B2 | 8/2018 | Carter | |
| D837,397 S | 1/2019 | Vellutato, Jr. | |
| 10,197,487 B2 | 2/2019 | Knollenberg et al. | |
| D847,365 S | 4/2019 | Vellutato, Jr. | |
| 10,309,876 B2 | 6/2019 | Takenaka et al. | |
| 10,330,578 B2 | 6/2019 | Manautou et al. | |
| 10,345,200 B2 | 7/2019 | Scialo et al. | |
| 10,371,620 B2 | 8/2019 | Knollenberg et al. | |
| 10,436,685 B2 | 10/2019 | Cherubini et al. | |
| 10,458,990 B1 | 10/2019 | Manautou et al. | |
| 10,571,369 B2 | 2/2020 | Vellutato, Jr. | |
| 10,684,209 B1 | 6/2020 | Manautou | |
| 10,792,694 B2 | 10/2020 | Gorbunov et al. | |
| 10,859,487 B2 | 12/2020 | Knollenberg et al. | |
| 10,908,059 B2 | 2/2021 | Knollenberg et al. | |
| 10,921,229 B2 | 2/2021 | Shamir | |
| 10,928,293 B2 | 2/2021 | Knollenberg et al. | |
| 10,997,845 B2 | 5/2021 | MacLaughlin et al. | |
| 2002/0174709 A1 | 11/2002 | Kim et al. | |
| 2003/0044771 A1 | 3/2003 | Anderson et al. | |
| 2003/0223912 A1 | 12/2003 | Knecht et al. | |
| 2005/0028593 A1 | 2/2005 | Rodier | |
| 2006/0272432 A1 | 12/2006 | Belongia et al. | |
| 2007/0010007 A1* | 1/2007 | Aysta | B01L 9/52 435/303.1 |
| 2007/0269849 A1 | 11/2007 | Bridenne et al. | |
| 2009/0078862 A1 | 3/2009 | Rodier et al. | |
| 2009/0111141 A1* | 4/2009 | Deutsch | C12M 23/12 435/307.1 |
| 2009/0190128 A1 | 7/2009 | Cerni et al. | |
| 2009/0197299 A1 | 8/2009 | Vargas et al. | |
| 2009/0268202 A1 | 10/2009 | Wagner | |
| 2009/0298129 A1 | 12/2009 | Spence et al. | |
| 2010/0062415 A1 | 3/2010 | Schwoebel et al. | |
| 2010/0171625 A1 | 7/2010 | Calio | |
| 2010/0212436 A1 | 8/2010 | Swenson et al. | |
| 2011/0132108 A1 | 6/2011 | Novosselov et al. | |
| 2011/0203931 A1 | 8/2011 | Novosselov et al. | |
| 2011/0267451 A1 | 11/2011 | Drescher et al. | |
| 2011/0301613 A1 | 12/2011 | Green | |
| 2013/0084597 A1 | 4/2013 | Rebe | |
| 2013/0260396 A1 | 10/2013 | Akcakir | |
| 2014/0132415 A1 | 5/2014 | Churchvara et al. | |
| 2015/0000595 A1 | 1/2015 | Gorbunov et al. | |
| 2015/0075301 A1* | 3/2015 | Scialo | A61K 35/51 73/863.22 |
| 2015/0210174 A1* | 7/2015 | Settele | B60L 53/14 320/109 |
| 2015/0259723 A1 | 9/2015 | Hartigan et al. | |
| 2016/0041074 A1 | 2/2016 | Pliskin et al. | |
| 2016/0126081 A1 | 5/2016 | Gorbunov | |
| 2016/0139013 A1 | 5/2016 | Gorbunov | |
| 2016/0305846 A1 | 10/2016 | Harivel et al. | |
| 2017/0336312 A1 | 11/2017 | Stoeber et al. | |
| 2019/0250785 A1 | 8/2019 | Pandolfi et al. | |
| 2019/0346345 A1 | 11/2019 | Scialo et al. | |
| 2020/0072729 A1 | 3/2020 | Lumpkin et al. | |
| 2020/0150017 A1 | 5/2020 | Bates et al. | |
| 2020/0150018 A1 | 5/2020 | Shamir | |
| 2020/0158603 A1 | 5/2020 | Scialo et al. | |
| 2020/0240896 A1 | 7/2020 | Karasikov et al. | |
| 2020/0355597 A1 | 11/2020 | Allan et al. | |
| 2020/0355599 A1 | 11/2020 | Rodier et al. | |

(56) References Cited

U.S. PATENT DOCUMENTS

| | | |
|---|---|---|
| 2021/0044978 A1 | 2/2021 | Michaelis et al. |
| 2021/0063349 A1 | 3/2021 | Rodier et al. |
| 2021/0102884 A1 | 4/2021 | MacLaughlin et al. |
| 2021/0136722 A1 | 5/2021 | Scialo et al. |
| 2021/0140867 A1 | 5/2021 | Knollenberg et al. |
| 2021/0190659 A1 | 6/2021 | Knollenberg et al. |
| 2021/0208054 A1 | 7/2021 | Ellis et al. |
| 2021/0295670 A1 | 9/2021 | MacLaughlin et al. |
| 2021/0381948 A1 | 12/2021 | Rodier et al. |
| 2022/0155212 A1 | 5/2022 | Rodier et al. |
| 2022/0228963 A1 | 7/2022 | Shamir |
| 2022/0236146 A1 | 7/2022 | Scialo et al. |
| 2022/0397495 A1 | 12/2022 | Yates et al. |
| 2022/0397510 A1 | 12/2022 | Yates et al. |
| 2022/0397519 A1 | 12/2022 | Knollenberg et al. |
| 2023/0009668 A1 | 1/2023 | Scialo et al. |
| 2023/0087059 A1 | 3/2023 | Knollenberg et al. |
| 2023/0112632 A1 | 4/2023 | Michaelis et al. |

FOREIGN PATENT DOCUMENTS

| | | |
|---|---|---|
| CN | 101528912 A | 9/2009 |
| CN | 101680874 A | 3/2010 |
| CN | 101755198 A | 6/2010 |
| CN | 102220235 A | 10/2011 |
| CN | 102460180 B | 5/2014 |
| CN | 105829860 A | 8/2016 |
| CN | 108956395 A | 12/2018 |
| CN | 109890309 A | 6/2019 |
| EP | 1175990 A1 | 1/2002 |
| EP | 1460126 A2 | 9/2004 |
| EP | 2279402 | 8/2015 |
| EP | 3025139 B | 4/2020 |
| JP | 2000-125843 A | 5/2000 |
| JP | 2000-337818 A | 12/2000 |
| JP | 2016-525688 A | 8/2016 |
| KR | 19990065286 A | 8/1999 |
| TW | 201526973 A | 7/2015 |
| TW | 201933427 A | 8/2019 |
| WO | WO 96/05040 A1 | 2/1996 |
| WO | WO 02/24279 A1 | 3/2002 |
| WO | WO 2007/144835 | 12/2007 |
| WO | WO 2011/059444 | 5/2011 |
| WO | WO 2015/013374 A1 | 1/2015 |
| WO | WO 2017/072591 A1 | 5/2017 |
| WO | WO 2018/050889 A2 | 3/2018 |
| WO | WO 2019/210375 | 11/2019 |
| WO | WO 2020/233854 A1 | 11/2020 |

OTHER PUBLICATIONS

Taiwan Search Report dated Mar. 20, 2023 in Taiwan application No. 110101936.
Adriani et al. (Feb. 1993) "Combined System for Observations of Tropospheric and Stratospheric Thin Clouds," *Journal of Atmospheric and Oceanic Technology* 10: 34-48.
Biswas et al. (1984), "High-velocity inertial impactors," *Environ. Sci. Technol.* 18(8): 611-616.
Chinese Office Action, English translation, and search report, dated Mar. 14, 2018, for corresponding Chinese application No. CN 201480052387.3, 30 pp.
Chinese Second Office Action, English translation, dated Nov. 8, 2018, in Chinese application No. CN 201480052387.3, 20 pp.
Chinese Decision of Rejection, English translation, dated Jul. 30, 2019, for corresponding Chinese application No. CN 201480052387.3, 27 pp.
Chinese Notice of Re-examination English translation, dated Dec. 14, 2020, in Chinese application No. CN 201480052387.3, 23 pp.
Dunkelberg et al. (2009) "Determination of the Efficacy of Sterile Barrier Systems Against Microbial Challenges During Transport and Storage," Infection Control and Hospital Epidemiology 30(2): 179-183.
European Examination Report, dated Jul. 18, 2018 in European application No. 14829610.6, 7 pp.
European Examination Report, dated Jan. 2, 2019 in European application No. 14829610.6, 5 pp.
European Examination Report, dated May 8, 2019 in corresponding European application No. 14829610.6, 7 pp.
European Examination Report, dated Aug. 26, 2021 in corresponding European application No. 20165176.7 5 pp.
Extended European Search Report dated May 22, 2017, for European Patent Application No. 14829610.6, 18 pp.
Extended European Search Report dated Jul. 15, 2020, for European Patent Application No. 20165176.7, 16 pp.
Extended European Search Report dated Dec. 15, 2021, for European Patent Application No. 19885202, 10 pp.
India First Examination Report, dated Jun. 11, 2020, for India Patent Application Serial No. 201617003349, 12 pp.
International Search Report and Written Opinion dated Nov. 6, 2014, for corresponding International Application No. PCT/US2014/047759, 14 pp.
International Search Report and Written Opinion, dated Jan. 27, 2020, corresponding to International Patent Application No. PCT/US2019/060574, 8 pp.
International Search Report and Written Opinion, dated Apr. 1, 2021, corresponding to International Patent Application No. PCT/US2021/013873, 9 pp.
Japanese Final Rejection, English Translation, dated Feb. 5, 2019 in Japanese Application No. 2016-529852, 2 pp.
Japanese Office Action and English translation, dated Apr. 10, 2018, for corresponding Japanese application No. JP 2016-529852, 6 pp.
Japanese Office Action and English translation dated Jul. 28, 2020 for corresponding Japanese application No. 2019-104831, 8 pp.
Japanese Office Action, dated Mar. 23, 2021, corresponding to Japanese Patent Application No. 2019-104831, 2 pp.
Korean Office Action and English machine translation dated Nov. 17, 2020 for corresponding Korean application No. 10-2016-7004698, 5 pp.
Korean Office Action, "Notice of Allowance," dated Dec. 29, 2020, corresponding to Korean Patent Application No. 10-2016-7004698, 3 pp.
Mitchell et al. (Sep. 1959) "Improved Cascade Impactor for . . . Measuring Aerosol Particle Sizes in air pollutants, commercial aerosols or cigarette smoke," *Industrial and Engineering Chemistry* 51(9): 1039-1042.
Partial Supplemental European Search report dated Feb. 7, 2017, for European Patent Application No. 14829610.6, 8 pp.
Particle Measuring Systems. 'DualCapt'. Datasheet, 2008. Retrieved online. [Retrieved on Oct. 6, 2014]. <URL:www.kenelec.com.au/sitebuilder/products/files/279/dual_capt.pdf>.
Taiwan office action dated Sep. 27, 2021 in Taiwan application No. 110101936, 6 pp.
U.S. Office Action, dated Aug. 11, 2016, in U.S. Appl. No. 14/338,615, 14 pp.
U.S. Office Action, dated Mar. 10, 2017, in U.S. Appl. No. 14/338,615, 15 pp.
U.S. Office Action, dated Jan. 5, 2018, in U.S. Appl. No. 14/338,615, 16 pp.
U.S. Office Action, dated May 11, 2018, in U.S. Appl. No. 14/338,615, 19 pp.
U.S. Office Action, dated May 1, 2019, in U.S. Appl. No. 14/338,615, 11 pp.
U.S. Office Action, dated Mar. 25, 2021, in U.S. Appl. No. 16/421,227, 6 pp.
U.S. Office Action, dated Jun. 7, 2021, in U.S. Appl. No. 16/421,227.
U.S. Office Action dated Aug. 9, 2021 in U.S. Appl. No. 16/678,687.
Taiwan Notice of Allowance and Search Report received in Taiwan Application No. 111150823 dated Nov. 17, 2023.

\* cited by examiner

ROBOTIC CONTROL FOR ASEPTIC PROCESSING

CROSS-REFERENCE TO RELATED APPLICATIONS

This application claims the benefit of priority to U.S. Provisional Patent Application No. 62/963,895, filed Jan. 21, 2020, which is hereby incorporated by reference in its entirety.

BACKGROUND OF INVENTION

This invention is in the field of particle sampling, collection and analysis. This invention relates generally to systems and methods for robotic sampling and counting systems for sampling particles from fluids in controlled environments.

Cleanrooms and clean zones are commonly used in semiconductor and pharmaceutical manufacturing facilities. For the semiconductor industry, an increase in airborne particulate concentration can result in a decrease in fabrication efficiency, as particles that settle on semiconductor wafers will impact or interfere with the small length scale manufacturing processes. For the pharmaceutical industry, where this type of real-time efficiency feedback is lacking, contamination by airborne particulates and biological contaminants puts pharmaceutical products at risk for failing to meet cleanliness level standards established by the U.S. Food and Drug Administration (FDA) and other foreign and international health regulatory agencies.

Humans being present in such environments increases the risk of particulate and biological contamination levels. Increasingly, controlled environment systems are moving towards automated or robotic systems in order to limit or eliminate human interaction. However, many applications requiring controlled environments also require or utilize environmental sampling to ensure that viable and non-viable particles and/or organisms remain below the desired levels.

Standards for the classification of cleanroom particle levels and standards for testing and monitoring to ensure compliance are provided by ISO 14664-1 and 14664-2. Aerosol optical particle counters are commonly used to determine the airborne particle contamination levels in cleanrooms and clean zones, and liquid particle counters are used to optically measure particle contamination levels in process fluids. Where microbiological particles are a particular concern, such as in the pharmaceutical industry, not only is quantification of the number of airborne particles important, but characterizing the viability and identity of microbiological particles is also at issue. ISO 14698-1 and 14698-2 provide standards for evaluation of cleanroom and clean zone environments for biocontaminants.

Currently, collection and analysis of airborne biological particles is commonly achieved using a variety of techniques including settling plates, contact plates, surface swabbing, fingertip sampling and impactor-based active air samplers. Cascade impactors have traditionally been used for collection and sizing of particles. In these devices, a series of accelerations and inertial impacts successively strip smaller and smaller particles from a fluid flow. Each stage of an inertial impactor operates on the principle that particles suspended in air can be collected by forcing a dramatic change in the direction of the particle-containing airflow, where the inertia of the particle will separate the particle from the airflow streamlines and allow it to impact on the surface. Biswas et al. describe the efficiency at which particles can be collected in a high velocity inertial impactor (Environ. Sci. Technol., 1984, 18(8), 611-616).

As requirements for lower viable and non-viable particle concentrations increase because of increased quality standards and governmental regulatory requirements there is a need for advancement in sampling technology in order to reduce false positives and reduce the risk of outside contamination from human interactions within the controlled environment.

It can be seen from the foregoing that there remains a need in the art for particle collection, analysis, and characterization systems for sampling and collecting particles and/or organisms from controlled environments with reduced human interaction in order to reduce the risk of further contamination. These systems may include collection any analysis of particles within components of a robotic restricted access barrier system or other automated controlled environmental processes.

SUMMARY OF THE INVENTION

Provided herein are systems and methods allowing for automated sampling and/or analysis of controlled environments, for example, to determine the presence, quantity, size, concentration, viability, species or characteristics of particles within the environment. The described systems and methods may utilize robotics or automation or remove some or all of the collection or analysis steps that are traditionally performed by human operators. The methods and systems described herein are versatile and may be used with known particle sampling and analysis techniques and devices including, for example, optical particle counters, impingers and impactors.

The provided systems and methods may be useful within controlled environments utilizing a robotic system, for example, robotically controlled restricted access barrier system (RABS) and positive pressure isolator systems. These systems and methods allow for integration with impactors in the controlled environment to position, connect, sample and/or analyze the environmental conditions within the controlled environment with little or no human contact, reducing the risk of contamination from particles or organisms present on operators. The described systems and methods may also allow for robotic sterilization of the environment or sampling components to further reduce or eliminate the risk of contamination.

The impactor may include a sampling head comprising one or more intake apertures, an impactor base connected to the sampling head, and a magnet fixed to the sampling head or the impactor base. The one or more intake apertures may allow for sampling a fluid flow containing particles. The impactor base may be operationally connected to receive at least a portion of the fluid flow from the sampling head. The impactor base may comprise an impact surface for receiving at least a portion of the particles in the fluid flow. The impactor base may comprise an outlet for exhausting the fluid flow. The sampling head and the impactor base may engage to enclose the impact surface.

The impact surface may be configured to receive and capture biological particles. The sampling head and the impactor base may engage to entirely enclose the impact surface, including for example, engaging via a substantially airtight seal. The sampling head and the impactor base may each independently comprise a polymer material. The impactor base and/or the sampling head may include a magnet for effective handling of the impactor by the robotic control system. At least a portion of the impactor base, sampling head, or both may be optically transparent.

The impact surface may comprise a growth medium for receiving biological particles in the fluid. The robotic control system may be configured to expose the impactor and/or the impact surface to the fluid. The robotic control system may be further configured to collect particles from the impactor and/or the impact surface. The robotic control system may be further configured to sample the particles from the fluid in the absence of a user physically contacting the impactor.

The impactor and/or the impact surface may comprise a growth medium for receiving biological particles in the fluid. Thus, the impactor base may comprise a growth medium positioned to receive the particles in the fluid flow, wherein the impact surface is a receiving surface of the growth medium. The robotic control system may be further configured for transporting the particle sampling or counting device to the sterilization system in a fully assembled configuration for sterilizing the particle sampling or counting device; and wherein the growth medium is present within the particle sampling or counting during sterilization thereof. Thus, in some embodiments, the impactor is configured for robotic sterilization of an outer surface of the impactor. In some embodiments, the impactor may be configured to be sterilized in a fully assembled configuration wherein the impact surface remains enclosed by the sampling head and impactor base.

In some embodiments, the particles collected by the impactor are microorganisms. In some embodiments, the impactor base, sampling head or both are optically transparent so as to allow visualization, optical detection or imaging of particles in the growth medium without physically accessing the growth medium.

The impactor may further comprise a selectively removable cover for covering the one or more intake apertures and thereby enclosing the impact surface. In some embodiments the one or more intake apertures may be disposed in a radial array on the sampling head and a magnet, sometimes referred to as a sampling head magnet, may be fixed to the sampling head in the center of the radial array.

In some embodiments, a magnet may be fixed to the selectively removable cover. In one embodiment the magnet is fixed to an underside of the selectively removable cover. For example, the magnet may be fixed to a protrusion of underside of the selectively removable cover.

In some embodiments, the magnet is a first cover magnet fixed to the underside of the selectively removable cover, wherein the impactor comprises a second cover magnet spaced apart from the first cover magnet and protruding from the underside of the selectively removable cover.

In those embodiments where one or more magnets are fixed to the cover, this magnet(s) may be referred to as a cover magnet(s). In such embodiments, the impactor may further comprise a sampling head magnet fixed to the sampling head. The sampling head magnet may be configured to mate with the cover magnet. Thus, in some embodiments, the selectively removable cover may be held in place due to the magnetic attraction of the sampling head magnet to the cover magnet.

The impactor may be configured for robotic manipulation via a robotic device. In one example, the robotic control system and the impactor may be configured for robotic removal of the selectively removable cover from the sampling head via a robotic device to expose the one or more intake apertures to an ambient environment. For example, the one or more magnets of the impactor may be configured to engage with a robotic device magnet of the robotic device. in some embodiments, the robotic device magnet may be an electromagnet. In some embodiments, the electromagnet may be configured to exert a greater magnetic attractive force on the cover magnet than the magnetic attractive force exerted on the cover magnet by the sampling head magnet, thereby allowing the robotic device to remove the cover. Thus, the robotic control system and the impactor may be configured for removal of the cover via engagement (e.g., magnetic attraction) of the robotic device magnet of the robotic device with the cover magnet.

The impactor may be further configured for robotic replacement of the selectively removable cover, via disengagement of the robotic device magnet from the cover magnet, to seal the impact surface off from to an ambient environment. In one embodiment, disengagement of the robotic device magnet may comprise reducing or cutting the power to the electromagnet.

In some embodiments, the sampling head and selectively removable cover engage via a compressible sealing member. In some embodiments, the compressible sealing member is an O-ring. In some embodiments, the impactor is configured to compress the compressible sealing member via magnetic attraction between the sampling head magnet and the cover magnet.

In some embodiments, the one or more magnets of the impactor may be fixed to a receiving surface of the impactor via an adhesive. In some embodiments, the magnet is cast into the sampling head or the impactor base. In some embodiments, the magnet is at least partially enclosed by a magnet chamber of the impactor.

In one embodiment, a method for sampling biological particles from a fluid flow comprises drawing a fluid flow through one or more intake apertures and into a sampling head of an impactor, wherein the fluid flow contains biological particles. At least some of the biological particles may be impacted onto an impact surface of an impactor base. The impactor base may engage the sampling head to enclose the impact surface. The fluid flow may be exhausted from the sampling head. The impactor or a component thereof may be manipulated via a magnet fixed to the impactor. At least a portion of the biological particles received by the impact surface may then be grown on the impact surface.

In some embodiments, the manipulating step occurs prior to the drawing a fluid step. In some embodiments, the manipulation step occurs after the growing step. In some embodiments, the manipulating step comprises robotic manipulation of the impactor or a component thereof via a robotic device. In some embodiments, the manipulating step comprises manual manipulation of the impactor or a component thereof via a magnetic hand tool. In some embodiments, the robotic manipulation comprises removing a selectively removable cover from the sampling head via a robotic device to expose the one or more intake apertures to an ambient environment. In some embodiments, the robotic manipulation comprises engaging the magnet of the impactor via a robotic device magnet of the robotic device. In some embodiments, the robotic manipulation comprises placing a selectively removable cover onto the sampling head via a robotic device to seal the impact surface off from to an ambient environment. In some embodiments, the robotic manipulation comprises sterilizing an outer surface of the impactor. In some embodiments, the robotic manipulation comprises sterilizing the impactor in a fully assembled configuration wherein the impact surface remains enclosed by the sampling head and impactor base.

A flow system for connection with the impactor may be integrated within a cleanroom or aseptic environment, wherein the robotic control system is further configured to sample the particles from the fluid under flow in the absence of a user being physically present in the cleanroom or aseptic environment. The robotic control system may be located inside of the cleanroom or aseptic environment, outside of the cleanroom or aseptic environment or partially located both inside and outside of the cleanroom or aseptic environment.

The provided method may further comprise a step of sterilizing the particle sampling or counting device, wherein the impact surface remains enclosed during sterilization, for example, to protect a growth media for capturing biological particles such as agar.

The provided method may further comprise a step of sterilizing the particle sampling or counting device in a fully assembled configuration, wherein the impact surface remains enclosed by the sampling head and base during sterilization. The sterilizing step may be performed by treating the fully assembled and enclosed particle sampling or counting device with at least one of: vaporized hydrogen peroxide, chlorine dioxide, ethylene oxide, moist heat, and dry heat.

The provided method may further comprise a step of culturing at least a portion of the biological particles received by the growth medium. The culturing step may allow for optical detection of the biological particles. The culturing step may be carried out without disassembling the fully assembled particle sampling or counting device.

The provided method may further comprise a step of characterizing the particles performed by the imaging device. The characterizing step may comprise, for example, determining a chemical composition of the particles or determining a particle size distribution of the particles.

The provided method may be performed in the absence of a user physically contacting the particle sampling or counting device. The fluid may originate and/or terminate in a cleanroom or aseptic environment; and wherein the method is performed in the absence of a user being physically present in the cleanroom or aseptic environment. Each of the providing step, flowing step, and/or receiving step, may be performed by the system configured for robotic control.

Devices and methods of the invention incorporate an integrated sampler and impact surface, such as the receiving surface of a growth media, in a manner to minimize, or entirely eliminate, risks associated with user handling, such as the occurrence of false positive determinations due to contamination of the impact surface during particle sampling, growth or analysis processes.

In some aspects, the invention provides a particle impactor device having an integrated sampler and enclosed impact surface designed for single use and/or disposable use, thereby eliminating the costs and contamination risks involved with reuse. Particle impactor devices of the present invention having an integrated sampler and enclosed impact surface are capable of achieving effective sampling and growth of biological particles while minimizing the incidence for user contamination during handling and use. Particle impactor devices of the present invention having an integrated sampler and enclosed impact surface are also capable of effective sterilization in a fully assembled configuration wherein the impact surface, such as the receiving surface of a growth medium, is maintained in an enclosed configuration during the sterilization process, thereby eliminating the need for a user to access the impact surface prior to particle sampling. The invention also provides optically transparent particle impactors capable of in situ optical and/or visual analysis of particles, such as viable biological particles, without the need for physical access or handling of the impact surface during sampling, growth and optical characterization of viable biological particles.

Impactor devices of the invention include single-use devices and/or disposable devices. Impactors of the invention are useful for monitoring biological particles in a cleanroom, aseptic or healthcare environment. Impactors of the invention are useful for sampling particles in a range of fluids including air or one or more process gases for a manufacturing application. Impactors of the invention are useful for sampling, growing and analyzing biological particles comprising viable microorganisms.

As described above, the impactor base comprises a growth medium positioned to receive the particles in the fluid flow, wherein the impact surface is a receiving surface of the growth medium. Useful growth media include culture medium, such as agar, broth, and other substrates, such as filters. In an embodiment, the growth medium is provided in a petri dish comprising an integrated component of the impactor base, for example, wherein the petri dish is cast in a single piece with the impactor base. In an embodiment, for example, the petri dish and impactor base comprise a single unitary element, such as a unitary component comprising a single cast polymer structure. In an embodiment, for example, the growth medium comprises an agar plate. In an embodiment, the sampling head and the impactor base engage, optionally reversibly, to entirely contain the impact surface, for example providing an airtight seal around the impact surface, thus only allowing fluid to pass through the intake apertures and interact with the impact surface.

As described above, the impactor may comprise a selectively removable cover provided on the sampling head for covering the intake apertures, thereby maintaining a sterile environment for the growth medium prior to sampling the fluid flow containing particles or for providing a hermetically sealed environment for the growth medium after sampling the fluid flow containing particles. In an embodiment, for example, the impactor base, sampling head or both are optically transparent so as to allow visualization, optical detection or imaging of particles in the growth medium without physically accessing the growth medium. In an embodiment, for example, the sampling head and the removable cover engage via a substantially airtight seal. In an embodiment, for example, the sampling head and the removable cover engage via a selectively removable interlocking connection. In an embodiment, for example, the sampling head and the removable cover engage via an O-ring connection, for example, provided between a bottom surface of the removable cover and a top surface of the sampling head.

Impactors of the invention may comprise a range of useful materials. In an embodiment, for example, the sampling head and the impactor base each independently comprise a polymer material, such as a synthetic or natural polymer. In an embodiment, for example, the sampling head and the impactor base each independently comprise a sterile material.

In an embodiment, for example, the outlet of the impactor base is connected to a fan or pump for providing the fluid flow through the impactor, wherein the flow changes direction after passing through the intake apertures.

The invention includes impactors comprising optically transparent components, for example, to allow for efficient use in a fully assembled configuration. In an embodiment, for example, at least a portion of the impactor base, sampling head or both are optically transparent to allow characterization of the particles on the impact surface without disengaging the sampling head and the impactor base. In an embodiment, for example, the impactor base, sampling head or both are optically transparent so as to provide a transmission greater than or equal to 50% for at least a portion of incident light having a wavelength from the range of 400 nm to 800 nm. In an embodiment, for example, the impactor base, sampling head or both are optically transparent so as to allow visualization, optical detection or imaging of particles on the impact surface without disengaging the sampling head and the impactor base. In an embodiment, for example, the impactor base, sampling head or both are optically transparent so as to allow determination of the amount of viable biological particles on the impact surface. In an embodiment, for example, the impactor base, sampling head or both are optically transparent so as to allow determination of the genus or species of viable biological particles on the impact surface.

In some embodiments, methods and devices of the invention provide a benefit of minimizing, or entirely eliminating, the need for a user to physically access the impact surface after sterilization. In an embodiment, for example, the method does not include a user physically contacting the growth medium after being contacted with the particles. In an embodiment, for example, a method of the invention further comprises the step of providing a cover on the sampling head for covering the intake apertures, thereby sealing the growth medium within the device after the sampling step.

In an embodiment, for example, the invention provides a method of sampling the fluid containing the particles using the impactor for a single use only, and optionally disposing of the impactor after use. In an embodiment, for example, the invention provides a method of monitoring biological particles in cleanroom or aseptic environments. In an embodiment, for example, the invention provides a method of monitoring biological particles in air or one or more process gases. In an embodiment, for example, a method of the invention further comprises repeating the steps of the method using a new sampler.

The devices and methods of the present invention are versatile and support a range of particle sampling, monitoring and analysis applications. For example, the present devices and methods are useful for applications involving preparation, handling, manufacture, storage, transfer, fill and/or finish of sterile pharmaceutical or biological agents, pharmaceutical or biological containers, pharmaceutical or biological delivery devices, medical devices including implantable devices, blood, cell and tissue materials. In addition, the present devices and methods are useful for monitoring and characterizing biological particles in healthcare environments, such as hospitals, operating rooms, surgical suites and compounding pharmacies. Other applications of the present devices and methods include the preparation, manufacture, storage, transfer or processing of cosmetics, personal care products, food and beverages.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Particle" refers to a small object which is often regarded as a contaminant. A particle can be any material created by the act of friction, for example when two surfaces come into mechanical contact and there is mechanical movement. Particles can be composed of aggregates of material, such as dust, dirt, smoke, ash, water, soot, metal, minerals, or any combination of these or other materials or contaminants. "Particles" may also refer to biological particles, for example, viruses, spores and microorganisms including bacteria, fungi, archaea, protists, other single cell microorganisms. Biological particles include, but are not limited to, microorganisms having a size on the order of 0.1-20 µm. Biological particles include viable biological particles capable of reproduction, for example, upon incubation within a growth media. A particle may refer to any small object which absorbs or scatters light and is thus detectable by an optical particle counter. As used herein, "particle" is intended to be exclusive of the individual atoms or molecules of a carrier fluid, for example, such gases present in air (e.g., oxygen molecules, nitrogen molecules, argon molecule, etc.) or process gases. Some embodiments of the present invention are capable of sampling, collecting, detecting, sizing, and/or counting particles comprising aggregates of material having a size greater than 50 nm, 100 nm, 1 µm or greater, or 10 µm or greater. Specific particles include particles having a size selected from 50 nm to 50 µm, a size selected from 100 nm to 10 µm, or a size selected from 500 nm to 5 µm.

The expression "sampling a particle" broadly refers to collection of particles in a fluid flow, for example, from an environment undergoing monitoring. Sampling in this context includes transfer of particles in a fluid flow to an impact surface, for example, the receiving surface of a growth medium. Alternatively sampling may refer to passing particles in a fluid through a particle analysis region, for example, for optical detection and/or characterization. Sampling may refer to collection of particles having one or more preselected characteristics, such as size (e.g., cross sectional dimension such as diameter, effective diameter, etc.), particle type (biological or nonbiological, viable or nonviable, etc.) or particle composition. Sampling may optionally include analysis of collected particles, for example, via subsequent optical analysis, imaging analysis or visual analysis. Sampling may optionally include growth of viable biological particles, for sample, via an incubation process involving a growth medium. A sampler refers to a device for sampling particles.

"Impactor" refers to a device for sampling particles. In some embodiments, an impactor comprises a sample head including one or more intake apertures for sampling a fluid flow containing particles, whereby at least a portion of the particles are directed onto an impact surface for collection, such as the receiving surface of a growth medium (e.g., culture medium such as agar, broth, etc.) or a substrate such as a filter. Impactors of some embodiments, provide a change of direction of the flow after passage through the intake apertures, wherein particles having preselected characteristics (e.g., size greater than a threshold value) do not make the change in direction and, thus, are received by the impact surface.

The expression "detecting a particle" broadly refers to sensing, identifying the presence of and/or characterizing a particle. In some embodiments, detecting a particle refers to counting particles. In some embodiments, detecting a particle refers to characterizing and/or measuring a physical characteristic of a particle, such as diameter, cross sectional dimension, shape, size, aerodynamic size, or any combination of these. A particle counter is a device for counting the number of particles in a fluid or volume of fluid, and optionally may also provide for characterization of the particles, for example, on the basis of size (e.g., cross sectional dimension such as diameter or effective diameter), particle type (e.g. biological or nonbiological), or particle composition. An optical particle counter is a device that detects particles by measuring scattering, emission or absorbance of light by particles.

"Flow direction" refers to an axis parallel to the direction the bulk of a fluid is moving when a fluid is flowing. For fluid flowing through a straight flow cell, the flow direction is parallel to the path the bulk of the fluid takes. For fluid flowing through a curved flow cell, the flow direction may be considered tangential to the path the bulk of the fluid takes.

"Fluid communication" refers to the arrangement of two or more objects such that a fluid can be transported to, past, through or from one object to another. For example, in some embodiments two objects are in fluid communication with one another if a fluid flow path is provided directly between the two objects. In some embodiments, two objects are in fluid communication with one another if a fluid flow path is provided indirectly between the two objects, such as by including one or more other objects or flow paths between the two objects. For example, in one embodiment, the following components of a particle impactor are in fluid communication with one another: one or more intake apertures, an impact surface, a fluid outlet, a flow restriction, a pressure sensor, a flow generating device. In one embodiment, two objects present in a body of fluid are not necessarily in fluid communication with one another unless fluid from the first object is drawn to, past and/or through the second object, such as along a flow path.

"Flow rate" refers to an amount of fluid flowing past a specified point or through a specified area, such as through intake apertures or a fluid outlet of a particle impactor. In one embodiment a flow rate refers to a mass flow rate, i.e., a mass of the fluid flowing past a specified point or through a specified area. In one embodiment, a flow rate is a volumetric flow rate, i.e., a volume of the fluid flowing past a specified point or through a specified area.

"Pressure" refers to a measure of a force exhibited per unit area. In an embodiment, a pressure refers to a force exhibited by a gas or fluid per unit area. An "absolute pressure" refers to a measure of the pressure exerted by a gas or fluid per unit area as referenced against a perfect vacuum or volume exerting zero force per unit area. Absolute pressure is distinguished from a "differential pressure" or "gauge pressure", which refers to a relative change or difference in force exhibited per unit area in excess of or relative to a second pressure, such as an ambient pressure or atmospheric pressure.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

FIGS. 1 are 5 are perspective exploded views of a particle impactor 10 and FIG. 2 is a side exploded view of the particle impactor 10. As shown in these figures, particle impactor 10 comprises a sampling head 200, a selectively removable cover 100 and an impactor base 300. The sampling head 200 includes a sampling head magnet 250 fixed to the underside of the sampling head 200. The selectively removable cover 100 includes a first cover magnet 155 and a second cover magnet 150 fixed to the underside of the cover 100, and spaced apart via spacer 158. The sampling head magnet 250 engages with the second cover magnet 150 in order to secure the cover 100 to the impactor. The sampling head 200 and the selectively removable cover 100 engage via compressible sealing member 110. The impactor 10 is configured to compress the compressible sealing member 110 via magnetic attraction between the sampling head magnet 250 and the second cover magnet 150. The sampling head 200 and the impactor base 300 engage via compressible sealing member 210. The first cover magnet 155 may be configured to engage with a robotic device.

The sampling head 200 includes a plurality of intake apertures 220 for sampling a fluid flow containing particles.

The impactor base 300 includes an outlet 320 and an impact surface 350. In operation, gas flow is directed through the intake apertures 220 of the sampling head 100 where it is accelerated towards the impact surface 350, and out the outlet 320 which forces the gas to rapidly change direction. Due to their momentum, particles entrained in the gas flow are unable to make the rapid change in direction and impact on the impact surface 350.

In embodiments, impact surface 350 comprises the receiving surface of a growth medium, such as agar, provided in impactor base 300. Viable biological particles collected on the impact surface, for example, can subsequently be grown and evaluated to provide an analysis of the composition of the fluid flow sampled. For collection of biological particles on the impact surface, control over the distance between the intake aperture 220 and the impact surface 350 is important. If the distance is too large, for example, the particles may sufficiently follow the fluid path so as to avoid impact with the impact surface 350. If the distance is too small, however, the particles may impact the impact surface 350 with a force sufficient to render the particles non-viable, and therefore unable to reproduce.

Figure 1:
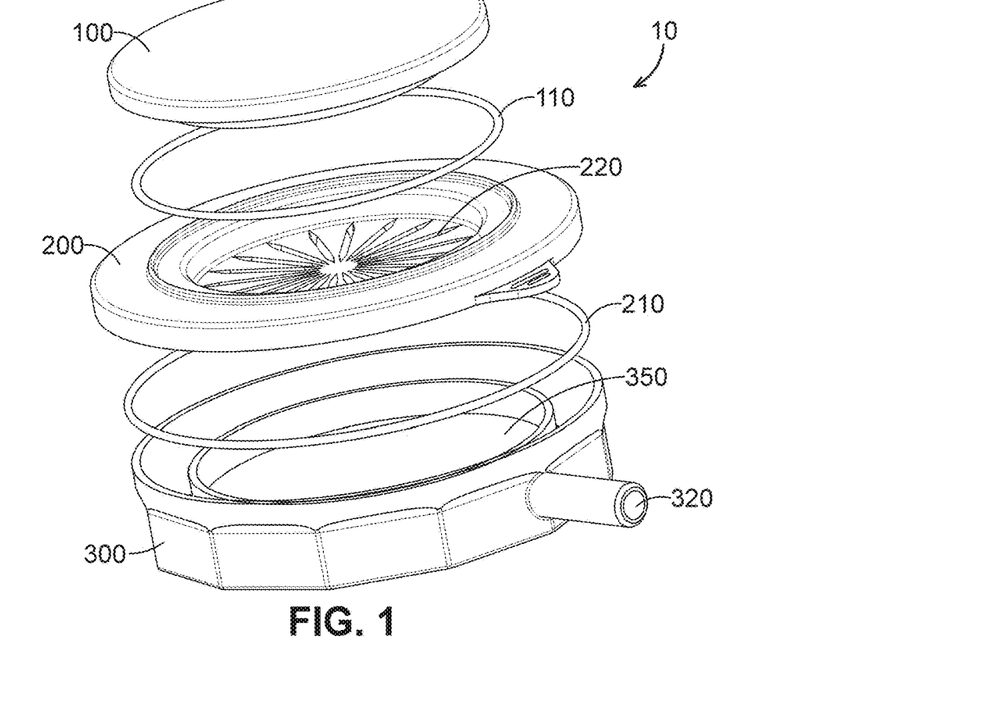
FIG. 1 is a perspective exploded view of an impactor of the present invention wherein components of the device are spatially separated for clarity.
Figure 2:
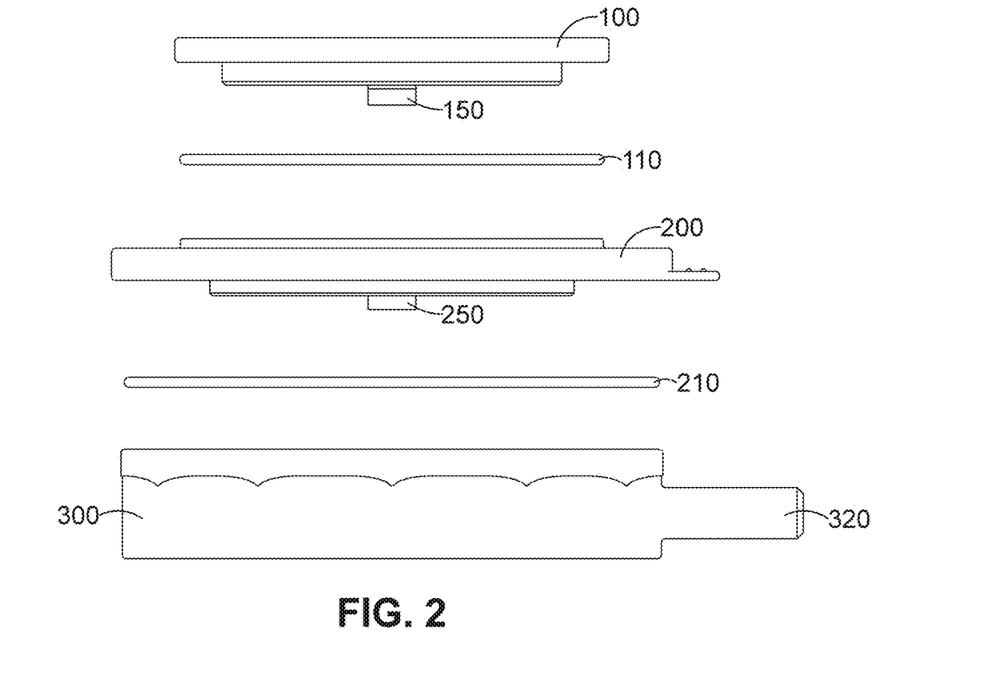
FIG. 2 is shows a side exploded view of the impactor of FIG. 1.
Figure 3A:
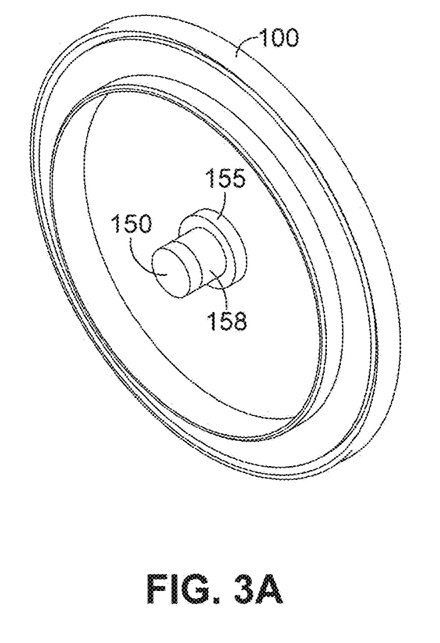
FIG. 3A shows a perspective view of a selectively removable cover of an impactor of the invention.
Figure 3B:
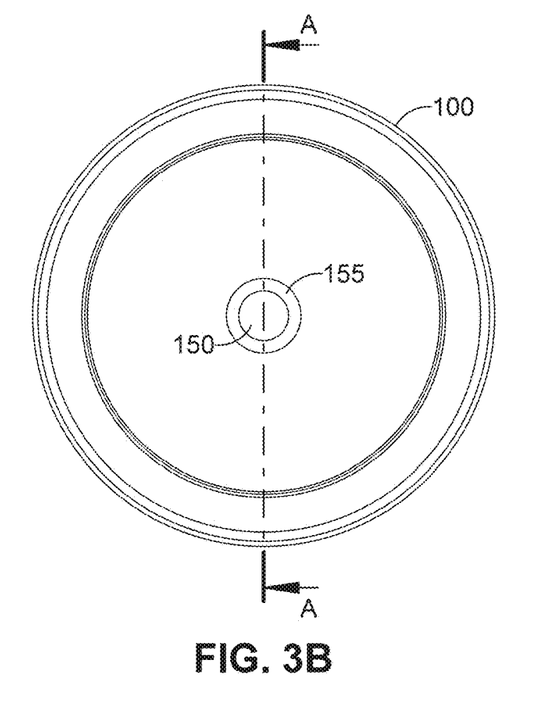
FIG. 3B shows a bottom view of the selectively removable cover of FIG. 3A.
Figure 3C:
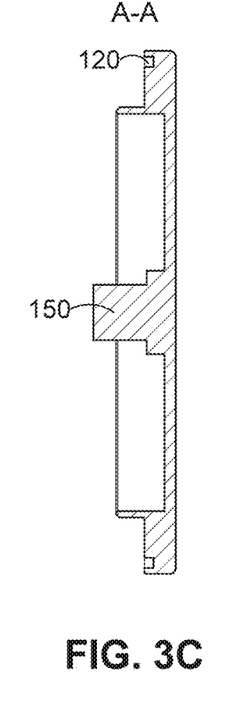
FIG. 3C shows a cross sectional view of the selectively removable cover of FIGS. 3A-B.

FIG. 3A shows a perspective view of selectively removable cover 100. FIG. 3B shows a bottom view selectively removable cover 100. FIG. 3C shows a cross sectional view of the selectively removable cover 100. Selectively removable cover 100 includes first and second cover magnets 155, 150 fixed to the center underside of cover 100 and separated by spacer 158.

Selectively removable cover 100 also includes an O-ring groove 120 on the underside of cover 100 proximal the outer edge. O-ring groove 120 is configured to receive O-ring 110. Second cover magnet 150 magnetically engages with sampling head magnet 250 to compress O-ring 110. Thus, the cover 100 may form an air tight seal with sampling head 200.

Figure 4A:
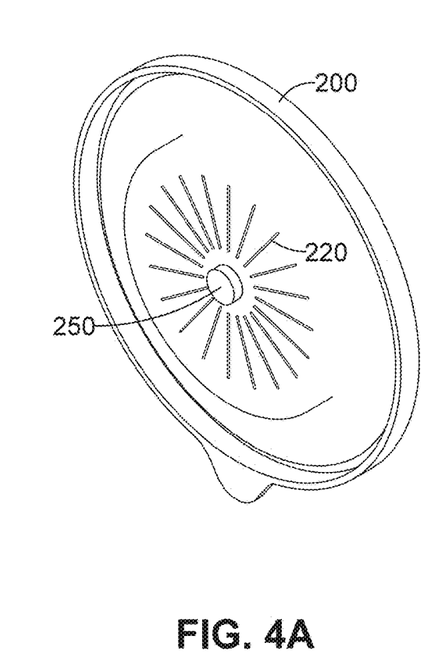
FIG. 4A shows a perspective view of a sampling head of an impactor of the invention.
Figure 4B:
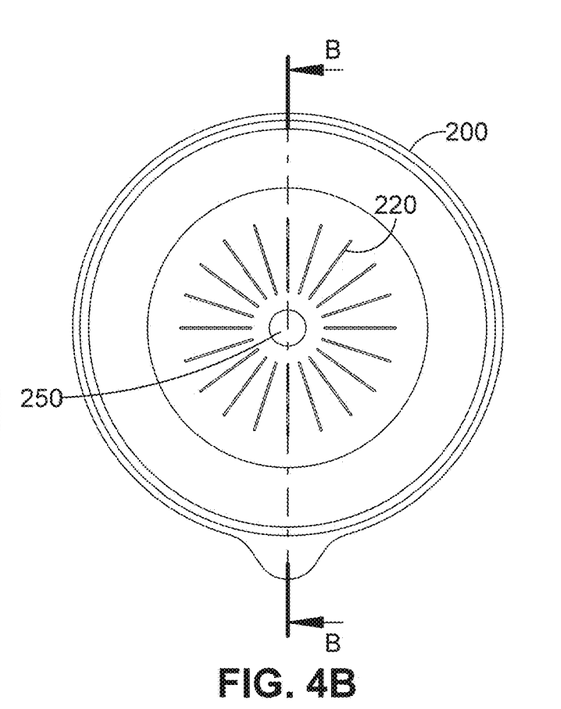
FIG. 4B shows a bottom view of the sampling head of FIG. 4A.
Figure 4C:
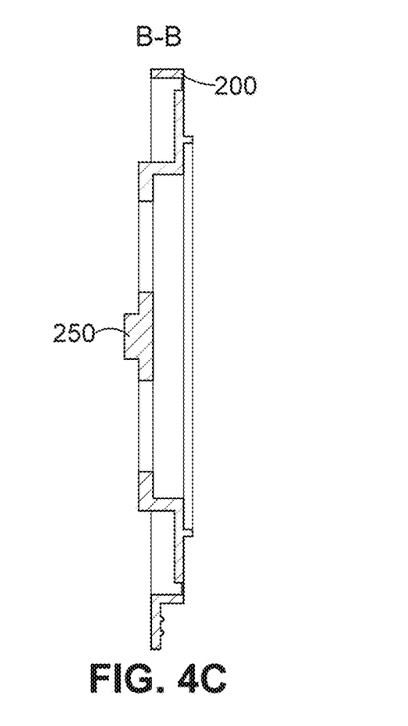
FIG. 4C shows a cross sectional view of the sampling head of FIGS. 4A-B.
Figure 5:
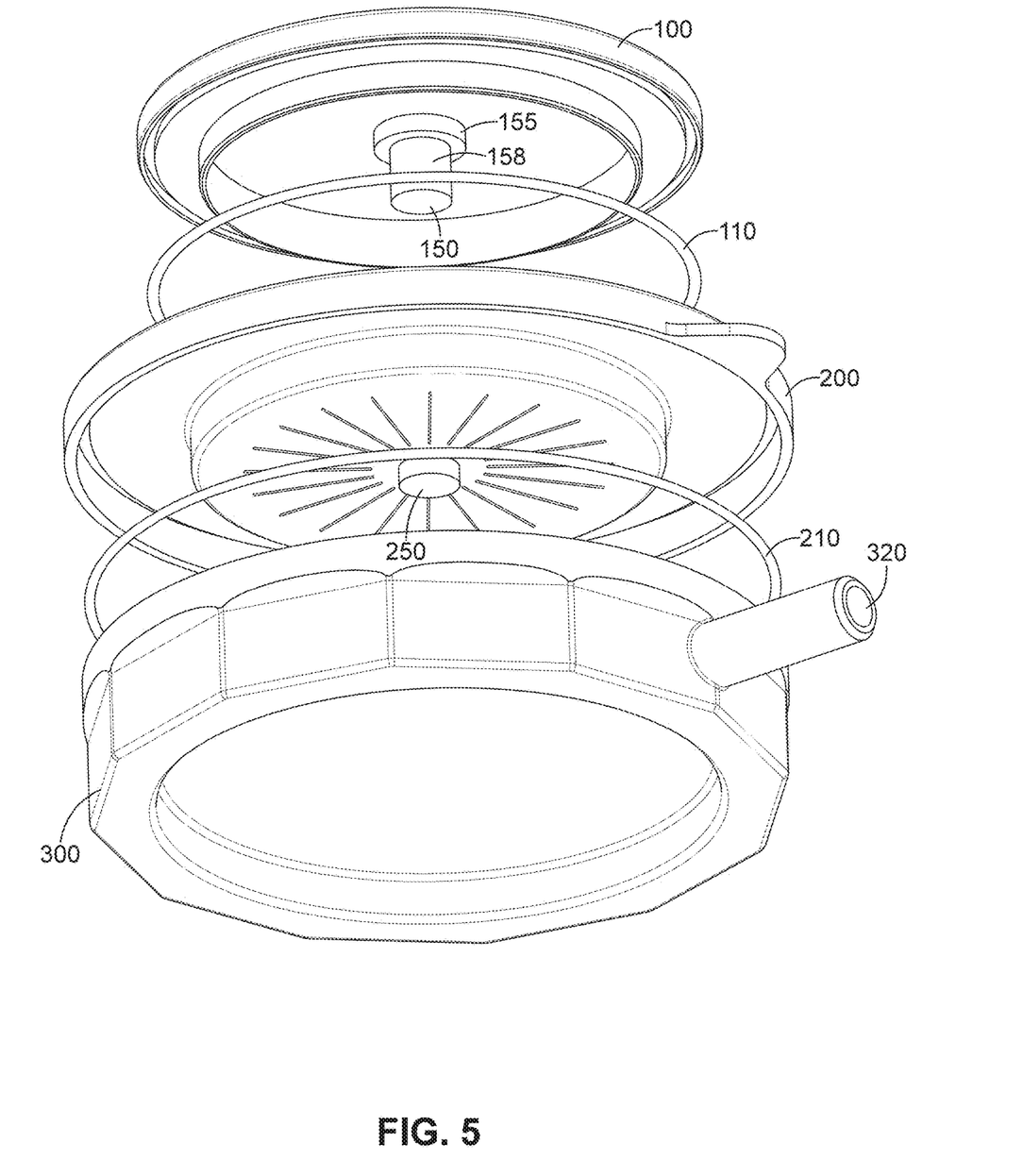
FIG. 5 is a different perspective exploded view of the impactor of FIG. 1.

FIG. 4A shows a perspective view of sampling head 200. FIG. 4B shows a bottom view of sampling head 200. FIG. 4C shows a cross sectional view of sampling head 200. Sampling head 200 includes apertures 220 and sampling head magnet 250. Apertures 220 may be arranged radially, as shown, around the sampling head magnet 250 in the center of the sampling head 200.

The invention provides air samplers, including impactors, for analysis of viable biological particles in an environment undergoing monitoring, such as an aseptic manufacturing environment. An aspect of the invention is an impactor device that integrates an agar media plate with an air sampler in an integrated single-use and/or disposable package. The present impactors are well adapted for use in cleanroom environments, particularly aseptic environments, where medical products are manufactured, such as sterile medicinal products (e.g., pharmaceuticals, biologicals, diagnostics, medical devices, medical implants, etc.). In an embodiment, for example, a connector on the side of the device supports connection of a vacuum source (e.g., portable vacuum source (e.g., pump or fan) or house vacuum line) that draws air into slit-shaped air inlets (e.g., 20 slits, 0.1 mm nominal width) where particles are subsequently impacted onto the receiving surface of a growth medium, such as agar media. After the cleanroom air is sampled, the device is transferred to a lab for incubation for multiple days to promote growth of viable microorganisms sampled. Lab technicians then count the number of CFU (colony forming units) and, if present, identify the genus or species of the microorganisms present.

Impactors of the invention provide a number of technical benefits including the following.

Elimination of false-positive contamination

With the conventional methods of microbial air sampling, the operators load an agar plate into a stainless steel sampling head device. In this process, the operators must directly contact the plate to load and unload the agar plate. When this process is carried out carefully and properly, the operator should not contaminate the media. However, it does routinely happen that the operator may contaminate the plate, creating a "false positive" (i.e. growth of microorganisms that did not come from the environment during the production batch, but from the handling by the operator before or after the production batch). When positive microbial growth is observed, the manufacturer's quality department must conduct an investigation to determine the level of risk to the finished drug product and decide whether to discard the batch or continue and ship the product. These investigations must be very thorough and are very costly (e.g., a quality investigation like this can cost the company anywhere from $5 K to $18 K per investigation). If the batch is discarded, it can result in losses of thousands to millions of dollars, depending on the market value of the product and the material and production costs of the product. In addition, false positives can also put the final patient at risk. In any investigation, human error can occur. Sometimes the quality department of a manufacturer may decide that a contamination event was a false positive, whereas actually it was real contamination that may compromise the purity of the drug product and put consumers/patients at risk of illness, injury or death.

The device of the present invention reduces, or essentially eliminates, the possibility of false-positive contaminants from operator handling. The configuration of the device allows for robotic handling including sterilization, sampling, incubation and/or analysis processes.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, and methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every combination of components described or exemplified herein can be used to practice the invention, unless otherwise stated.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. An impactor comprising:
   a sampling head comprising one or more intake apertures for sampling a fluid flow containing particles and a selectively removable cover for covering the one or more intake apertures; and
   an impactor base operationally connected to receive at least a portion of the fluid flow from the sampling head; the impactor base comprising an impact surface for receiving at least a portion of the particles in the fluid flow and an outlet for exhausting the fluid flow;
   a first cover magnet fixed to an underside of the selectively removable cover; and
   a second cover magnet spaced apart from the first cover magnet and protruding from the underside of the selectively removable cover;
   wherein the sampling head and the impactor base engage to enclose the impact surface.

2. The impactor of claim 1, the impactor comprising:
   a sampling head magnet fixed to the sampling head, the sampling head magnet configured to mate with the second cover magnet.

3. The impactor of claim 2, wherein the one or more intake apertures are disposed in a radial array on the sampling head, and wherein the sampling head magnet is fixed to the sampling head in the center of the radial array.

4. The impactor of claim 1, wherein an impactor base magnet is fixed to the impactor base.

5. The impactor of claim 1, further comprising a sampling head magnet fixed to the sampling head, the impactor comprising:
   an impactor base magnet fixed to the impactor base.

6. The impactor of claim 1 wherein the sampling head and selectively removable cover engage via a compressible sealing member.

7. The impactor of claim 6, wherein the impactor is configured to compress the compressible sealing member via magnetic attraction between the sampling head magnet and the cover magnet.

8. The impactor of claim 7, wherein the compressible sealing member is an O-ring.

9. The impactor of claim 1, wherein the an impactor base magnet is fixed to a receiving surface of the impactor via an adhesive.

10. The impactor of claim 1, wherein an impactor base magnet is cast into the sampling head or the impactor base.

11. The impactor of claim 1, wherein an impactor base magnet is at least partially enclosed by a magnet chamber of the impactor.

12. The impactor of claim 1, wherein the impactor is configured for robotic manipulation via a robotic device.

13. The impactor of claim 1, wherein the first cover magnet is configured to engage with a robotic device magnet of a robotic device.

14. The impactor of claim 1, wherein the impactor is configured for robotic removal of the selectively removable cover from the sampling head via a robotic device to expose the one or more intake apertures to an ambient environment.

15. The impactor of claim 1, wherein the impactor is configured for robotic replacement of a selectively removable cover onto the sampling head via a robotic device to seal the impact surface off from to an ambient environment.

16. The impactor of claim 1, wherein the impactor is configured for robotic sterilization of an outer surface of the impactor.

17. The impactor of claim 1, wherein the particles are microorganisms.

18. The impactor of claim 1, wherein the impactor base further comprises a growth medium positioned to receive the particles in the fluid flow, wherein the impact surface is a receiving surface of the growth medium.

19. The impactor of claim 18, wherein the impactor base, sampling head or both are optically transparent so as to allow visualization, optical detection or imaging of particles in the growth medium without physically accessing the growth medium.

20. The impactor of claim 1, wherein the impactor is configured to be sterilized in a fully assembled configuration wherein the impact surface remains enclosed by the sampling head and impactor base.

21. A method for sampling biological particles from a fluid flow, the method comprising:

drawing a fluid flow through one or more intake apertures and into a sampling head of an impactor, wherein the fluid flow contains biological particles;

impacting at least some of the biological particles onto an impact surface of an impactor base, the impactor base engaging the sampling head to enclose the impact surface;

exhausting the fluid flow from the sampling head;

manipulating the impactor or a component thereof via a magnet fixed to the impactor, wherein the manipulating comprises manual manipulation of the impactor or a component thereof via a magnetic hand tool; and growing at least a portion of the biological particles received by the impact surface.

22. The method of claim 21, wherein the manipulating step occurs prior to the drawing a fluid step.

23. The method of claim 21, wherein the manipulation step occurs after the growing step.

* * * * *